(12) United States Patent
Chiu et al.

(10) Patent No.: US 7,019,142 B2
(45) Date of Patent: *Mar. 28, 2006

(54) PROCESS FOR PREPARING NAPHTHYRIDONES AND INTERMEDIATES

(75) Inventors: Charles K. Chiu, New York, NY (US); Lewin T. Wint, New York, NY (US)

(73) Assignee: Pfizer Inc., New York, NY (US)

( * ) Notice: Subject to any disclaimer, the term of this patent is extended or adjusted under 35 U.S.C. 154(b) by 163 days.

This patent is subject to a terminal disclaimer.

(21) Appl. No.: 10/087,756

(22) Filed: Mar. 4, 2002

(65) Prior Publication Data

US 2002/0095043 A1    Jul. 18, 2002

Related U.S. Application Data

(62) Division of application No. 09/718,324, filed on Nov. 22, 2000, now abandoned, which is a division of application No. 09/236,737, filed on Jan. 25, 1999, now Pat. No. 6,184,380.

(60) Provisional application No. 60/071,601, filed on Jan. 16, 1998.

(51) Int. Cl.
    *C07D 471/02* (2006.01)

(52) U.S. Cl. ........................................... 546/123

(58) Field of Classification Search ............... 546/122, 546/123
    See application file for complete search history.

(56) References Cited

U.S. PATENT DOCUMENTS

| | | | |
|---|---|---|---|
| 5,102,667 A | 4/1992 | Dubroeucq et al. | 424/489 |
| 5,164,402 A * | 11/1992 | Brighty | 514/300 |
| 5,229,396 A | 7/1993 | Brighty | 514/300 |
| 5,298,629 A | 3/1994 | Braish | 548/452 |
| 5,391,763 A | 2/1995 | Brighty | 548/515 |
| 5,475,116 A | 12/1995 | Brighty et al. | 548/452 |
| 5,623,078 A | 4/1997 | Urata et al. | 548/452 |
| 5,728,711 A | 3/1998 | Girard et al. | 514/300 |
| 5,763,454 A | 6/1998 | Handanyan et al. | 514/300 |
| 5,847,158 A | 12/1998 | Lawson | 548/513 |
| 5,929,240 A | 7/1999 | Braish et al. | 546/123 |
| 6,066,647 A * | 5/2000 | Douglas et al. | 546/123 |
| 6,184,380 B1 * | 2/2001 | Chiu et al. | 546/123 |
| 6,194,424 B1 * | 2/2001 | Eckenberg et al. | 514/292 |

FOREIGN PATENT DOCUMENTS

| | | | |
|---|---|---|---|
| EP | 0230274 | | 7/1987 |
| EP | 0413455 | | 2/1991 |
| EP | 0818445 | | 1/1998 |
| EP | 0930297 A1 * | | 1/1998 |
| EP | 0930297 | * | 12/1999 |
| HU | 0211681 | | 12/1995 |
| HU | P9402530 | | 1/1999 |
| SU | 1538897 | | 1/1990 |
| WO | WO 9102526 | | 3/1991 |
| WO | WO 9318001 | | 9/1993 |
| WO | WO 97/00268 | * | 1/1997 |
| WO | WO 9707800 | | 3/1997 |
| WO | 9707800 | * | 6/1997 |
| WO | WO 9719921 | | 6/1997 |
| WO | WO 9906368 | | 11/1999 |

OTHER PUBLICATIONS

US 1998-7160 P, Patent Application, "Process for preparing napthyridones and intermediates", Chiu et. al., pp. 1-7.*
Kiso, et. al. , "A Flouride Ion Deprotection strategy in Peptide synthesis, combination with selective deprotection using the Dilute Methanesulfonic acid of alpha-amino protecting groups", Col. 36 (1988), Chem. Pharm. Communications, pp. 5024-5027.*
Bundgaard, et al., Design of prodrugs, Elsevier, pp. 27-30.*
Braish et al., "Construction of the (1 alpha, 5 alpha, 6 alpha)-6-amino-3-azabicyclo[3.1.0]hexane Ring System," Synlett, 11, pp. 1100-1102 (1991).

* cited by examiner

*Primary Examiner*—D. Margaret Seaman
(74) *Attorney, Agent, or Firm*—Gregg C. Benson; Lance Y. Liu

(57) ABSTRACT

A process for preparing a naphthyridone carboxylic acid and its derivatives makes use of side chain intermediates of formulae I and IV herein.

4 Claims, No Drawings

PROCESS FOR PREPARING NAPHTHYRIDONES AND INTERMEDIATES

This is a division of application Ser. No. 09/718,324, filed Nov, 22, 2000 now abandoned, which is a divisional of application Ser. No. 09/236,737, filed Jan. 25, 1999, now U.S. Pat. No. 6,184,380, which claimed the benefit of U.S. Provisional Application No. 60/071,601, filed Jan. 16, 1998, all of which are hereby incorporated herein by reference.

This invention relates to a process for preparing the naphthyridone carboxylic acid, trovafloxacin and derivatives thereof, and intermediates of use therein.

Trovafloxacin has the formula

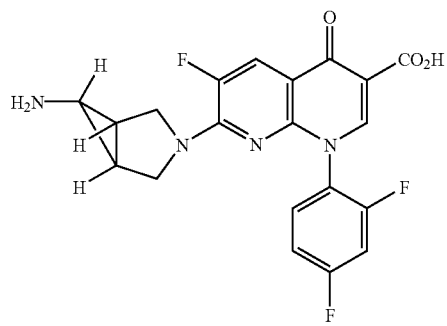

VII as disclosed in U.S. Pat. No. 5,164,402. The patent also discloses processes for making the compound by using an intermediate of the formula

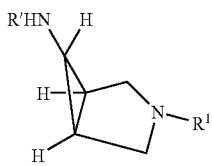

wherein R' is a nitrogen protecting group, such as tertiary butyloxycarbonyl.

U.S. Pat. No. 5,475,116 discloses the preparation of other intermediates for use in preparing the naphthyridones of U.S. Pat. No. 5,164,402.

The present invention relates to a process for preparing a compound of the formula

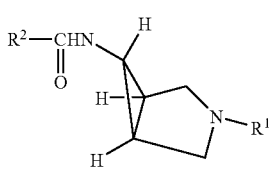

I wherein $R^1$ is benzyl, wherein the phenyl of the benzyl may be substituted by one or more of $C_1$–$C_6$ alkyl, $C_1$–$C_6$ alkoxy, halo, nitro, amino or trifluoromethyl, and $R^2$ is $C_1$–$C_6$ alky, trifluoromethyl, or phenyl which may be substituted by one or more of $C_1$–$C_6$ alkyl, $C_1$–$C_6$ alkoxy, halo, nitro, amino or trifluoromethyl, which comprises (a) reducing a compound of the formula

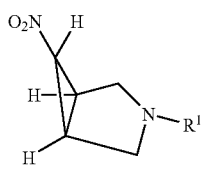

II wherein $R^1$ is as defined above, in the presence of iron and a organic solvent under acidic conditions, and (b) acylating the compound of formula III formed:

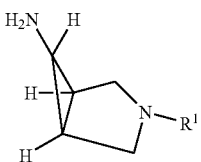

III with an acylating agent of the formula $R^2C(O)X$ wherein $R^2$ is as defined above, and X is a leaving group.

In a prefered embodiment of the invention, the compound of formula III formed in step (a) is not isolated before acylation step (b).

The invention is further related to a process for preparing a compound of the formula

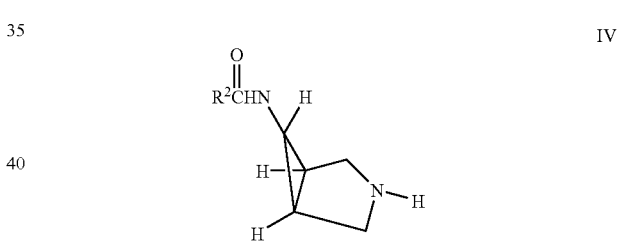

IV by debenzylating the compound of formula I wherein $R^1$ and $R^2$ are as defined above.

In a preferred embodiment, the debenzylation is carried out by reacting a compound of formula I with hydrogen and palladium catalyst in acetic acid and an organic solvent.

The invention also relates to reacting a compound of the formula IV with a compound of the formula

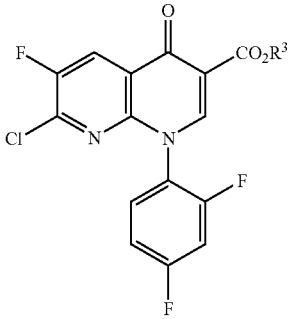

V wherein $R^3$ is $C_1$–$C_6$ alkyl, to form a compound of the formula

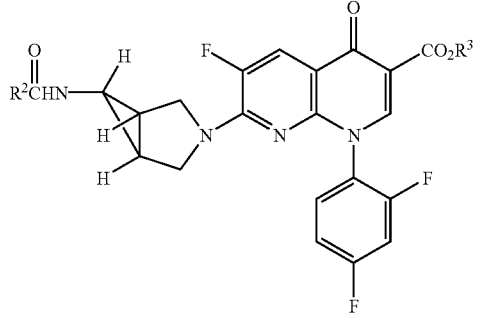

wherein $R^2$ is as defined above with reference to formula I.

The invention relates to hydrolyzing the compound of formula VI with methanesulfonic acid, water and an organic solvent to form the monomethanesulfonic acid salt of the compound of the formula VII, trovafloxacin.

The invention also relates to hydrolysis of the compound of formula VI with methanesulfonic acid and $R^3$OH wherein $R^3$ is as defined above to form the monomethanesulfonic acid salt of the compound of the formula

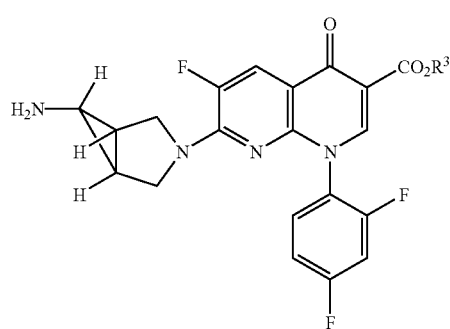

The invention further relates to the intermediates of the formulae

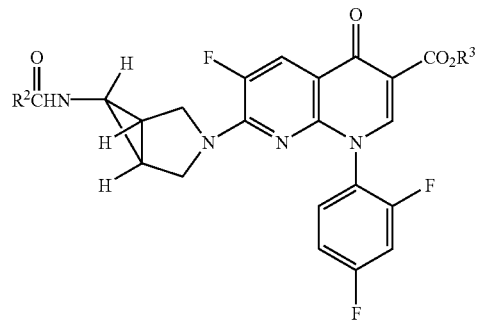

wherein $R^2$ is $C_1$–$C_6$ alkyl, trifluoromethyl, or phenyl which may be substituted by one or more of $C_1$–$C_6$ alkyl, $C_1$–$C_6$ alkoxy, halo, nitro, amino or trifluoromethyl, and
$R^3$ is $C_1$–$C_6$ alkyl, and

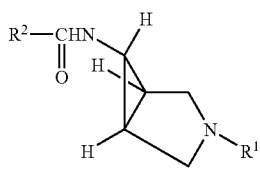

wherein
$R^1$ is hydrogen (see formula IV) or benzyl, wherein the phenyl of the benzyl may be substituted by one or more of $C_1$–$C_6$ alkyl, $C_1$–$C_6$ alkoxy, halo, nitro, amino or trifluoromethyl, and
$R^2$ is $C_1$–$C_6$ alkyl, trifluoromethyl, or phenyl which may be substituted by one or more of $C_1$–$C_6$ alkyl, $C_1$–$C_6$ alkoxy, halo, nitro, amino or trifluoromethyl.

The term "alkyl", as used herein, includes saturated monovalent hydrocarbon radicals having straight, branched or cyclic moieties, e.g. methyl, ethyl.

The term "alkoxy", as used herein, includes O-alkyl groups wherein "alkyl" is defined above.

The processes of the invention are depicted in the following reaction scheme. Unless indicated otherwise, $R^1$, $R^2$, $R^3$ and X are as defined above.

Reaction Scheme

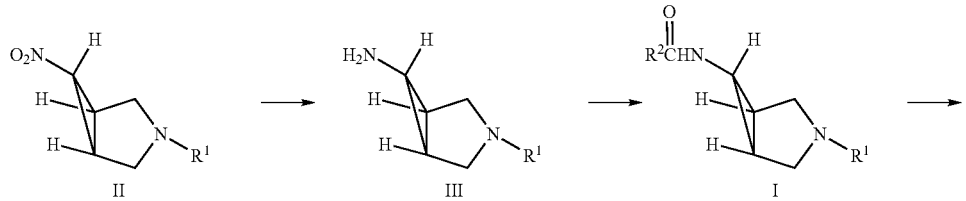

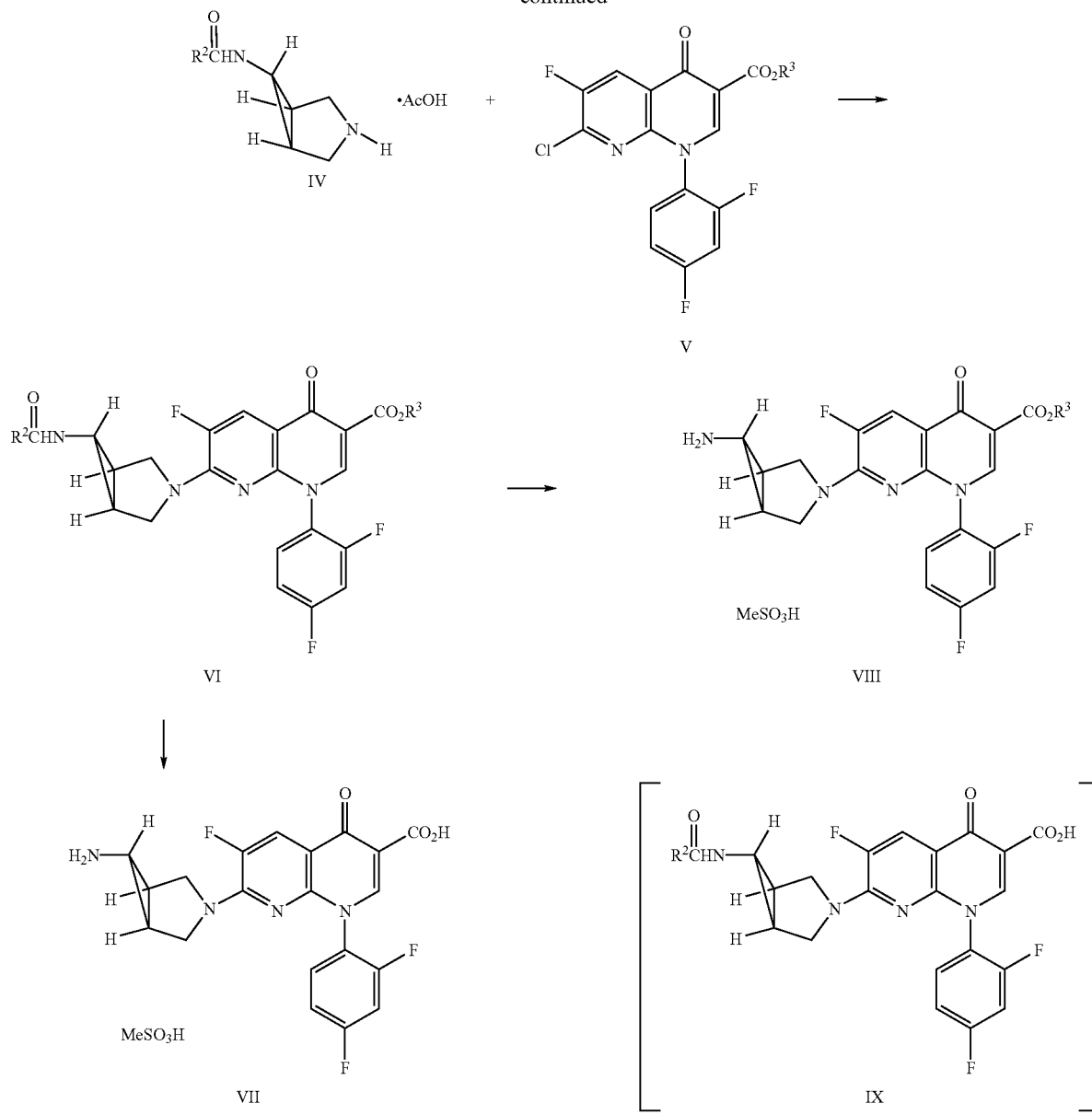

The compound of formula III is prepared from the corresponding compound of formula II by reduction in the presence of iron and an organic solvent under acidic conditions. The organic solvent is a $C_1$–$C_6$ alcohol, such as ethanol, or an ether such as tetrahydrofuran (THF), and preferably, an alcohol. The acidic conditions are obtained by use of a mineral acid, such as hydrochloric acid, or an organic acid, such as acetic acid (AcOH). Acetic acid is preferred since it generally results in increased yields.

The compound of formula III may then be isolated from the reaction mixture or may be reacted further in situ, without isolation from the reaction mixture. In either case, the further processing is by acylation with an acylating agent of the formula $R^2C(O)X$ to form the compound of formula I. The leaving group X is conveniently a halogen, such as chloro, or the acetoxy group. If the compound of formula III is first isolated, then the acylation may be conducted under conventional acylating conditions, for instance, in the presence of an organic solvent of the type discussed above.

The compound of formula I is subjected to debenzylation to form the compound of formula IV. It is understood that in the context of the invention, debenzylation includes removal of $R^1$ wherein $R^1$ is benzyl or substituted benzyl. The reaction proceeds in accordance with conventional debenzylation of tertiary nitrogen, conveniently by use of hydrogen and palladium catalyst in acetic acid, and in an organic solvent. The organic solvent may be a $C_1$–$C_6$ alcoholic solvent, such as ethanol, ethyl acetate, THF or water, or a mixture thereof, such as ethanol and water.

The compound of formula VI is obtained by coupling the corresponding compound of formula IV with the bicyclic intermediate ester of formula V. This coupling reaction may be conducted with or without a solvent. The solvent, when used, must be inert under the reaction conditions. Suitable solvents are ethyl acetate, acetonitrile, tetrahydrofuran, ethanol, chloroform, dimethylsulfoxide, pyridine, and water, and mixtures thereof.

The reaction temperature usually ranges from about 20° C. to about 150° C.

The reaction may advantageously be carried out in the presence of an acid acceptor such as an inorganic or organic base, e.g. an alkali metal or alkaline earth metal carbonate or bicarbonate, or a tertiary amine, e.g. triethylamine, pyridine or picoline.

The mesylate salt of the compound of formula VII, trovafloxacin, is formed by hydrolysis of the compound of formula VI with methanesulfonic acid, water and an organic solvent. Examples of suitable organic solvents include a $C_1$–$C_6$ alcohol, acetone, dimethoxy ethane, glyme, THF, N-methyl-pyrrolidinone, and water, and mixtures thereof.

The mesylate salt of the compound of formula VIII is obtained by hydrolysis of the compound of formula VI with methanesulfonic acid and a $C_1$–$C_6$ alcohol of the formula $R^3OH$, for example ethanol. The compound of formula VIII is an intermediate in the preparation of the mesylate salt of a prodrug of trovafloxacin wherein the amino group is substituted by an amino acid or a polypeptide, e.g. dipeptide, as disclosed in U.S. Pat. No. 5,164,402.

The compound of formula IX in the Reaction Scheme is the intermediate formed in the reaction from compound VI to VII.

The compound of formula VII and the mesylate salt thereof (the active compounds) are useful in the treatment of bacterial infections of broad spectrum, particularly the treatment of gram-positive bacterial strains.

The active compounds may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm. They can be injected parenterally, for example, intramuscularly, intravenously or subcutaneously. For parenteral administration, they are best used in the form of a sterile aqueous solution which can contain other solutes, for example, enough salt or flucose to make the solution isotonic. In the case of animals, compounds can be administered intramuscularly or subcutaneously at dosage levels of about 0.1–50 mg/kg/day, advantageously 0.2–10 mg/kg/day given in a single daily dose or up to 3 divided doses.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The following Examples illustrate the invention. The abbreviations used mean the following: GC=gas chromatography; MS=mass spectometry; TLC=thin layer chromatography, HPLC=high performance liquid chromatography; LCMS=liquid chromatography mass spectometry; and NMR=nuclear magnetic resonance.

EXAMPLE 1

(1α, 5α, 6α)-6-Acetamido-3-benzyl-3-azabicyclo [3.1.0]hexane

A 3-necked round bottom flask, equiped with a thermometer, a overhead stirrer and a condenser with nitrogen purge, was charged with 768 g of nitrocyclopropane, 5.75 L of isopropanol (7.5 volumes), 1.79 L of acetic acid (9.1 equivalents) and 1153 g of iron powder (6 equivalents). The reaction mixture was heated at 50° C. until the reaction was completed by GC/MS analysis (about 6 hours). 448 mL of acetic anhydride (1.4 equivalents) was added and stirred at 50° C. for 15 minutes before cooling. The reaction mixture was diluted with 8 L isopropanol (10.5 volumes) and stirred for 30 minutes. The residual iron was filtered off and the cake washed with 11.25 L of isopropanol (15 volumes). The isopropanol solution was concentrated in vacuo to an oil, 18 L of dichloroethane (24 volumes) was added before bringing the pH to 12 with 8.8 L of 5% sodium hydroxide solution (about 12 volumes). The layers were separated and the separated organic layer was dried by magnesium sulfate. The resulting dark amber oil was treated with 7.5 L of hexanes (10 volumes) and granulated at 25° C. before collecting the product as a white solid. Drying at 50° C. under vacuum gave 610 g of the title compound (77% yield). Analysis was done by GC/MS, NMR and TLC.

EXAMPLE 2

(1α, 5α, 6α)-6-Acetamido-3-azabicyclo[3.1.0]hexane

A Parr Bottle was charged with 150 g of the compound of Example 1, 112 mL of acetic acid (3 equivalents), 1.5 L of methanol (10 volumes) and 15 g of (10% by wt. 50% wet) Pd/C catalyst (0.1 equivalent). The bottle was purged with nitrogen and then brought to 50 psi pressure with hydrogen. The mixture was shaken for 48 hours and recharged with catalyst as necessary during the debenzylation reaction. After TLC indicated that the reaction was complete, the catalyst was filtered off, and the filtrate was concentrated in vacuo to an oil. 3 L of ethyl acetate (20 volumes) was added to the oil, and granulated for an hour. The solid was collected by filtration and dried under vacuum at 50° C. to provide 107 g of the title compound (82% yield) as the acetic acid salt

EXAMPLE 3

(1α, 5α, 6α)-7-(6-acetamido-3-azabicyclo[3.1.0] hex-3-yl)-1-(2,4-difluorophenyl)-6-fluoro-1,4-dihydro-4-oxo-1,8-naphthyridine-3-carboxylic acid, ethyl ester A reaction flask was charged with 241.9 g of 7-chloro-6-fluoro-1,4-dihydro-4-oxo-1,8-naphthyridine-3-carboxylic acid ethyl ester, 151.6 g of the acetic acid salt of the compound of Example 2 (1.2 equivalents), 2661 mL of ethyl acetate (11 volumes) and 220 mL of triethylamine (2.5 equivalents). The mixture was heated at refluxing temperature under nitrogen for 6 hours monitored by HPLC or LCMS. After the reaction was completed, the reaction mixture was cooled to ambient temperature. Water (11 volumes) was added and the biphasic mixture was stirred for 17 hours. The white solid was collected by filtration, washed with 2661 mL of water (12 volumes) and oven dried at 50° C. to provide 292 g of the title compound (95% yield).

EXAMPLE 4

In a reaction flask, 220 g of the compound of Example 3, 1.76 L of n-butanol (8 volumes), 1.54 L of water (7 volumes) and 141 mL of 70% methanesulfonic acid (3.0 equivalents) were mixed. The mixture was heated at reflux for 21 hours, and the reaction was monitored by HPLC or LCMS. After complete reaction, the mixture was cooled to 50° C. and filtered to make it speck-free. The filtrated was cooled to 0–5° C. and granulated for 2 hours. The solid was collected by filtration, washed with 220 mL of water (1 volume) and 660 mL n-butanol (3 volumes). The wet cake was mixed with 660 mL of n-butanol (3 volumes), seeded with 0.1 gm of the desired polymorph and heated to 95–100° C. After complete polymorph conversion, in approximately 2 hours, the mixture was cooled to ambient temperature. The solid was filtered, washed with 100 mL of n-butanol (0.5 volumes) and dried in a nitrogen atmosphere to provide 200 g of (1α, 5α, 6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxylic acid, monomethanesulfonate (87% yield).

EXAMPLE 5

0.8 mL of methanesulfonic acid (2.7 equivalents) was added dropwise to a solution of 2.2 g of the compound of Example 3 in 10 mL of ethanol (4.5 volumes). The resulting reaction mixture was heated at refluxing temperature for 40 hours, monitored by GCMS. After the reaction was completed, it was diluted with ethyl acetate (20 mL) and washed with (3×10 ml) 1M sodium hydroxide solution. The organic layer was separated, dried over anhydrous magnesium sulphate and filtered. The filtrate was concentrated in vacuo to provide 1.37 g of (1α, 5α, 6α)-7-(6-amino-3-azabicyclo [3.1.0]hex-3-yl)-1-(2,4-difluorophenyl)-6-fluoro-1,4-dihydro-4-oxo-1,8-naphthyridine-3-carboxylic acid ethyl ester, monomethanesulfonate (96% yield).

The invention claimed is:

1. A process for the preparation of a compound of the formula

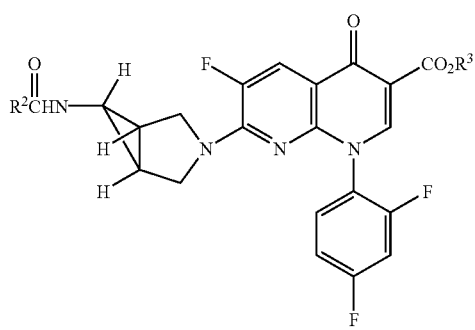

VI wherein $R^2$ is $C_1$–$C_6$ alkyl, trifluoromethyl, or phenyl which may be substituted by one or more of $C_1$–$C_6$ alkyl, $C_1$–$C_6$ alkoxy, halo, nitro, amino or trifluoromethyl, and $R^3$ is $C_1$–$C_6$ alkyl, which comprises reacting a compound of the formula

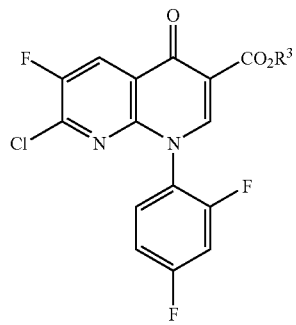

V with a compound of the formula

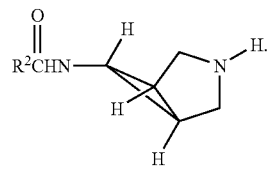

IV

2. A process comprising hydrolysis of the compound of formula VI with methanesulfonic acid, water and an organic solvent to form a monomethanesulfonic acid salt of a compound of the formula

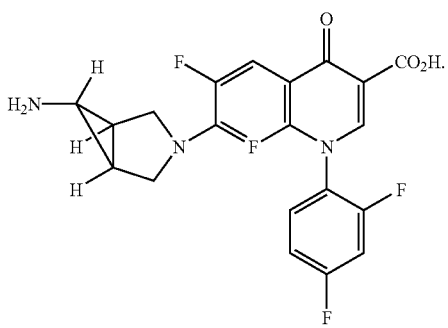

VII

3. A process comprising hydrolysis of the compound of formula VI with methanesulfonic acid and $R^3OH$ wherein $R^3$ is $C_1$–$C_6$ alkyl to form a monomethanesulfonic acid salt of a compound of the formula

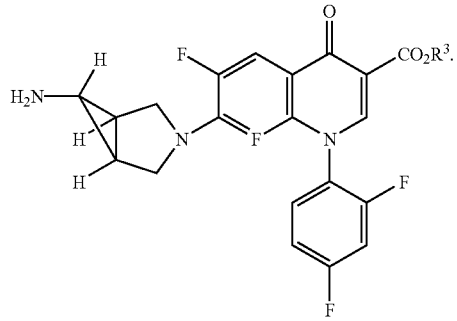

VIII

4. A compound of the formula

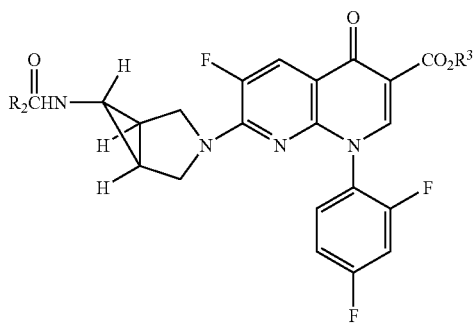

VI wherein
  $R^2$ is $C_1$–$C_6$ trifluoromethyl, or phenyl which may be substituted by one or more of $C_1$–$C_6$ alkyl, $C_1$–$C_6$ alkoxy, halo, nitro, amino or trifluoromethyl, and
  $R^3$ is $C_1$–$C_6$ alkyl.

* * * * *